United States Patent [19]

Lwoff et al.

[11] 4,401,114
[45] Aug. 30, 1983

[54] APPARATUS FOR HEATING OF THE NASAL PASSAGES

[75] Inventors: André Lwoff, Paris, France; Aharon Yerushalmi; Irun R. Cohen, both of Rehovot, Israel; Gideon B. Moshe, Rishon Le Zion, Israel

[73] Assignee: Yeda Research & Development Co., Ltd., Rehovot, Israel

[21] Appl. No.: 252,263

[22] Filed: Apr. 8, 1981

Related U.S. Application Data

[63] Continuation-in-part of Ser. No. 930,182, Aug. 1, 1978, abandoned.

[30] Foreign Application Priority Data

| Sep. 8, 1977 [IL] | Israel | 52690 |
| Aug. 4, 1978 [GB] | United Kingdom | 32263/78 |
| Aug. 8, 1978 [DE] | Fed. Rep. of Germany | 2834622 |
| Aug. 8, 1978 [JP] | Japan | 53/96563 |
| Sep. 8, 1978 [FR] | France | 78 23409 |

[51] Int. Cl.³ .............................................. A61M 16/00
[52] U.S. Cl. .............................. 128/200.14; 128/200.21; 128/203.27; 128/204.17
[58] Field of Search .................. 128/203.17, 203.26, 128/203.27, 204.17, 200.21, 368, 400, 401, 203.16

[56] References Cited

U.S. PATENT DOCUMENTS

| 125,965 | 4/1872 | Leonard | 128/200.21 |
| 742,244 | 10/1903 | Sherburne | 128/200.14 |
| 865,021 | 9/1907 | Dorment | 128/200.21 |
| 1,554,219 | 9/1925 | Kitchen | 128/200.21 |
| 1,832,916 | 11/1931 | Purdie | 128/203.27 |
| 2,040,630 | 5/1963 | Silten | 128/200.21 |
| 2,242,085 | 5/1941 | Peirano | 128/203.16 |
| 2,906,463 | 9/1959 | Curry | 128/200.22 |
| 3,903,883 | 9/1975 | Pecina et al. | 128/203.27 |
| 3,949,743 | 4/1976 | Shanbrom | 128/203.17 |
| 4,038,980 | 8/1977 | Fodor | 128/203.27 |

FOREIGN PATENT DOCUMENTS

| 150117 | 2/1937 | Austria | 128/200.21 |
| 261779 | 3/1949 | Switzerland | 128/200.21 |
| 1107780 | 3/1968 | United Kingdom . | |
| 1242694 | 8/1971 | United Kingdom . | |
| 1294808 | 11/1972 | United Kingdom . | |
| 1343385 | 1/1974 | United Kingdom . | |
| 1448473 | 9/1976 | United Kingdom . | |
| 1475710 | 6/1977 | United Kingdom . | |
| 1490974 | 11/1977 | United Kingdom . | |

Primary Examiner—Henry J. Recla
Attorney, Agent, or Firm—Browdy & Neimark

[57] ABSTRACT

Apparatus for treatment of the common cold or allergic rhinitis including apparatus for providing a heated and humidified stream of gas at a precisely controlled temperature at a location spaced from a patient's nostrils. According to a preferred embodiment the stream is provided at a temperature of 43° C. plus or minus 0.5° C. A corresponding technique for treatment is also provided.

7 Claims, 2 Drawing Figures

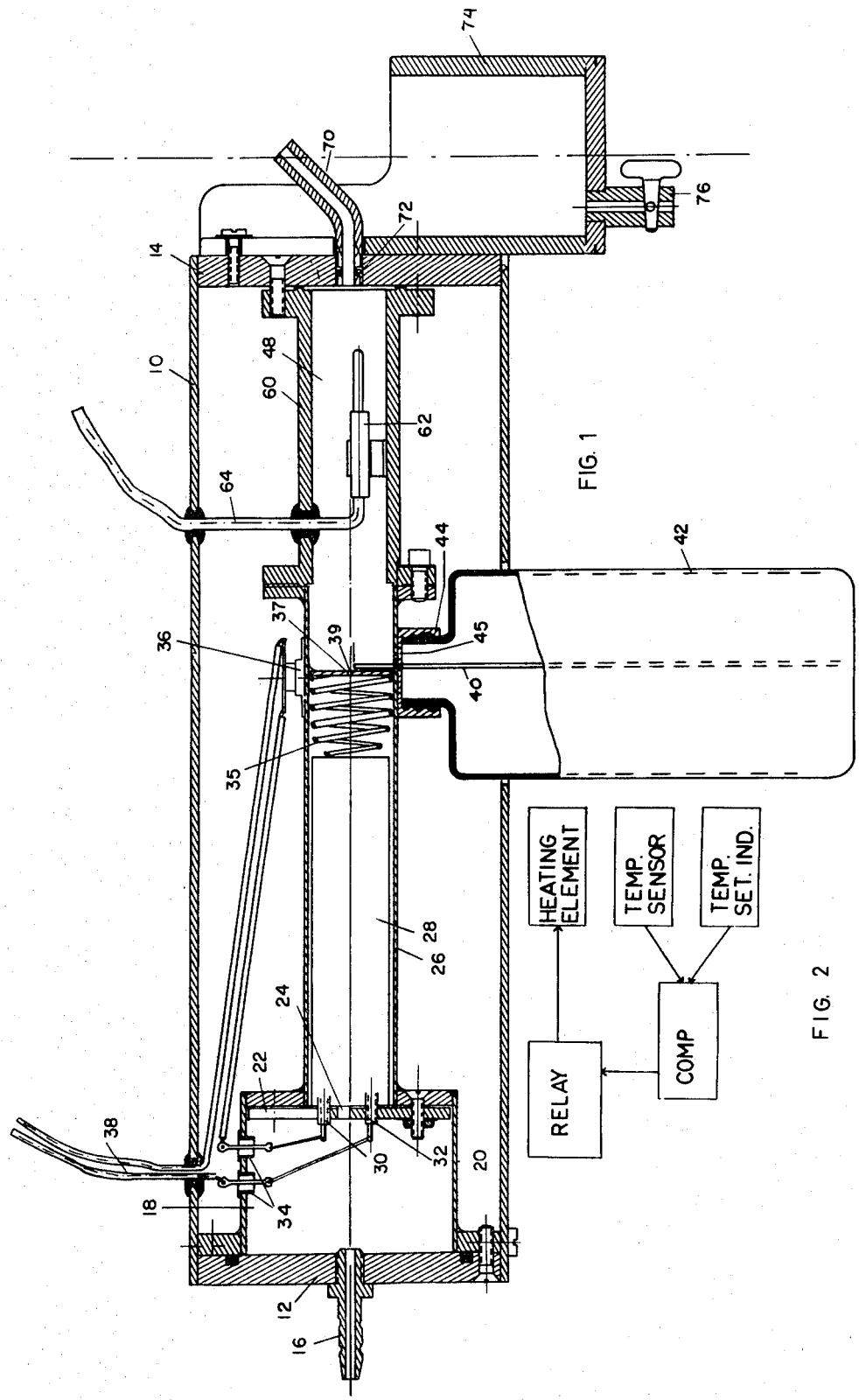

APPARATUS FOR HEATING OF THE NASAL PASSAGES

This a continuation-in-part of U.S. patent application Ser. No. 930,182 filed Aug. 1, 1978, now abandoned.

FIELD OF THE INVENTION

The present invention relates to medical apparatus and techniques generally, and more particularly to apparatus and methods for the treatment of the common cold, allergic rhinitis and other ailments associated with the nasal mucosa.

BACKGROUND OF THE INVENTION

It has been shown by André Lwoff that a small increase in temperature above the optimum can stop viral development and eventually lead to the destruction of a virus. A general review on temperature and viruses has been published in an article entitled "La Virulencia de Los Virus Y La Lucha del Organismo Contra La Infeccion Viral" (Spanish), Fundacion F. Cuenca Villoro Instituto de Investigacion Ulta Zaragoza, 1974. The present inventors are not aware, however, of applications of these theories to the treatment of the nasal mucosa, nor to the treatment of a common cold or allergic rhinitis connected with the nasal mucosa.

Various forms of apparatus are known for supplying heated and humidified air to patient for inhalation therapy. Examples of such apparatus are described in U.S. Pat. No. 3,903,883 to Pecina, U.S. Pat. No. 2,040,630 to Silten, U.S. Pat. No. 1,832,916 to Purdie, U.S. Pat. No. 742,244 to Sherburne, U.S. Pat. No. 865,021 to Dorment, Swiss Pat. No. 261,779, Austrian Pat. No. 150,117, U.S. Pat. No. 1,554,219 to Kitchen, U.S. Pat. No. 2,906,463 to Curry and British Pat. Nos. 1,490,974; 1,475,710; 1,448,473; 1,343,385; 1,294,808; 1,242,694; and 1,110,780.

The prior art apparatus of which applicants are aware and which is mentioned hereinabove is generally intended to supply air for inhalation purposes in response to a breathing in action by a patient and is not designed to provide a flow of humidified hot air to the nasal mucosa. In the examples where temperature controls are provided, they are intended to preserve a temperature range wherein no damage to the patient occurs and are not designed to maintain a precise temperature at the nasal passages. In none of the prior art apparatus is there a teaching or suggestion that such apparatus is suitable for treatment of the common cold, or for the treatment of allergic rhinitis. In fact, none of the prior art apparatus mentioned above is suitable for treatment of the nasal mucosa, allergic rhinitis or the common cold.

The temperature of the gas stream provided by prior art apparatus is too low to affect the viruses causing the common cold or to affect the conjugate factor leading to allergic rhinitis. Such apparatus is not suitable for heating the nasal passages and the nasal mucosa homogeneously at 43° C. and without causing damage to the nasal mucosa.

SUMMARY OF THE INVENTION

The present invention seeks to provide apparatus and a technique for treatment of the common cold and allergic rhinitis through the supply of heated humidified air to the nasal mucosa.

For the purpose of the present specification and claims the term "common cold" will be used to describe a medical condition known more scientifically as viral rhinitis.

There is thus provided in accordance with an embodiment of the present invention apparatus for treatment of the common cold or allergic rhinitis including apparatus for providing a heated and humidified stream of gas at a precisely controlled temperature at a location spaced from a patient's nostrils, the kinetic energy of the stream of gas being selected such that it reaches the nasal mucosa of a patient without requiring inhalation by the patient. Additionally, in accordance with an embodiment of the present invention, the volume of gas supplied to the patient's nostrils is approximately 33 liters per minute.

In accordance with a preferred embodiment of the present invention, the outlet temperature of the stream of heated and humidified gas is maintained at 43° Centigrade plus or minus 0.5° Centigrade.

Additionally in accordance with an embodiment of the present invention the apparatus is provided with means for positioning the patient's nostrils at least one centimeter from the providing location.

Further in accordance with an embodiment of the invention there is provided a method for treatment of allergic rhinitis or the common cold comprising the provision of heated humidified air to the patient's nostrils at approximately 43° Centigrade.

BRIEF DESCRIPTION OF THE DRAWINGS

The present invention will be more fully understood and appreciated from the following detailed description taken in conjunction with the drawings in which:

FIG. 1 is a schematic illustration of apparatus for treatment of the common cold and allergic rhinitis constructed and operative in accordance with an embodiment of the present invention; and FIG. 2 is a block diagram illustration of temperature sensing circuitry useful in the embodiment of FIG. 1.

DETAILED DESCRIPTION OF A PREFERRED EMBODIMENT

Referring now to FIGS. 1 and 2 there is seen apparatus for providing a stream of heated and humidified air to the nasal mucosa comprising a housing 10, typically formed of plastic such as P.V.C. and first and second end members 12, and 14, also typically formed of a plastic material. A gas inlet port 16 is provided for receiving a supply of gas under pressure. Alternatively compressor apparatus may be provided for providing the desired supply of pressurized gas. Normally the gas supplied is air.

Gas inlet port 16 communicates through an appropriately sized aperture formed in end member 12 with an inlet chamber 18 which is typically maintained at a pressure of between 2.0 and 2.25 Kg/cm$^2$. Chamber 18 is defined by a side wall 20 and an end wall 22. End wall 22 is apertured to define a passageway 24 from chamber 18 to a channel 26 in which is disposed an electrical heating element 28. Heating element 28 is coupled to a source of electrical current via conductors 30 and 32 which extend inside chamber 18 and through pressure seals 34 in wall 20 for connection, in series to a contact thermostat 36 and to a power cable 38, which is connected to an electric power source (not shown), via suitable control circuitry which will be described hereinafter in connection with FIG. 2.

Channel 26 terminates in an apertured end wall 37 defining a narrow fluid passage 39 typically of 1 mm diameter for the passage of a narrow stream of pressurized gas therethrough. A spring 35 is disposed between heating element 28 and end wall 37 to hold the heating element securely in position despite vibrations which occur naturally during operation thereof. Just beyond and below passage 39 is located the open end of a liquid supply tube 40 which communicates with the interior of a liquid container 42 in which water or any other suitable liquid may be provided.

Container 42 is supported by a threaded mounting member 44 attached to cylinder 26. Mounting member 44 is apertured to define a communication passageway 45 between the interior of container 42 and a chamber 48 which is defined by a channel 60.

The stream of hot air passing over the opening of liquid supply tube 40 causes liquid to be drawn out of the tube and to be effectively broken into small droplets, i.e. sonicated, and sprayed in the air.

The hot wet air produced in chamber 48 impinges upon a temperature sensor 62, such as a thermistor or thermocouple, connected by electrical cable 64 to suitable control circuitry (not shown). This control circuitry, which will be described in connection with FIG. 2 governs the operation of the heating element 28 in accordance with the temperature sensed at sensor 62. The temperature regulated wet air emerges from chamber 48 via a pair of exhaust nozzles 70 which are positioned adjacent but not in touching relationship to a subjects's nostrils. Nozzles 70 extend through end wall 14 via a suitably sized aperture formed therein, and are sealed with respect thereto by sealing rings 72.

Disposed below the outlet of nozzles 70 is a drip collector 74 having a drain cock 76.

It is noted that collector 74 provides an opportunity for oversize drops to settle downwards and not to enter the patient's nostrils. According to a preferred embodiment of the present invention the average droplet size is 4–8 microns.

Reference is now made to FIG. 2 which shows in schematic illustration, temperature control circuitry for use with the apparatus above described. A comparator 80 receives inputs from a manually settlable temperature set indicator 82 which may conveniently be in the form of a dial. Comparator 80 also receives an input from temperature sensor 62 (FIG. 1) which measures the actual temperature of the hot wet air being dispensed. In response to the difference between the two indicated temperatures, comparator 80 provides an electrical signal to relay means 84 which in turn operates the heating element 28 (FIG. 1) at such temperature and at such time intervals as is necessary to maintain a desired air temperature within a desired range.

It is a particular feature of the invention that the apparatus is operated to provide heated humidified air at a temperature of 43° Centigrade ±0.5° Centrigrade. The application of heated humidified air to a patient at this temperature to patients has been found in clinical tests to provide long term relief from symptoms of common cold and certain types of allergies such as allergic rhinitis.

It will be appreciated by persons skilled in the art that the invention is not limited to what has been shown and described herein. Rather the scope of the present invention is defined only by the claims which follow.

We claim:

1. Apparatus for the treatment of the common cold or allergic rhinitis comprising:

controllable apparatus located in a first enclosure for providing a stream of heated pressurized gas;

means for humidifying the stream of gas for providing a stream of heated and humidified gas including water droplets having an average droplet size of 4–8 microns;

means for governing the temperature of said heated and humidified stream of gas to maintain the temperature at 43 degrees centigrade plus or minus 0.5 degrees centigrade;

means having an outlet for directing an unconfined volume of said heated and humidified gas around the nasal mucosa of a patient without requiring inhalation by the patient; and means for maintaining an unconfined minimum separation of 1 cm between said outlet and the nostrils of a patient.

2. Apparatus for treatment of the common cold or allergic rhinitis according to claim 1 wherein the controllable apparatus provides a stream of gas at a pressure selected such that when the stream impinges on the nasal mucosa its pressure is near zero.

3. Apparatus for treatment of the common cold or allergic rhinitis according to claim 1 and wherein said means for directing provides said stream of heated and humidified gas to the nasal mucosa with a predetermined amount of kinetic energy sufficient to enable said stream to reach said nasal mucosa but not ordinarily sufficient to enable it to reach therebeyond in the absence of inhalation by the patient.

4. Apparatus according to claim 1 and wherein said apparatus is operative to deliver said stream of heated and humidified gas at a rate of 33 liters per minute.

5. A method for treatment of the common cold or allergic rhinitis comprising the steps of:

providing a stream of heated pressurized gas from an apparatus;

humidifying the stream of gas for providing a stream of heated and humidified gas including water droplets of an average droplet size of 4–8 microns;

maintaining the temperature of said heated and humidified stream of gas at 43 degrees centigrade plus or minus 0.5 degrees centigrade;

directing an unconfined volume of said heated and humidified gas around the nasal mucosa of a patient without requiring inhalation by the patient; and maintaining an unconfined minimum separation of 1 cm between apparatus said outlet of said and the nostrils of a patient.

6. A method for treatment according to claim 5 and wherein said gas is air.

7. A method according to claim 5 and wherein said providing step comprises the step of providing 33 liters per minute of said stream of gas.

* * * * *